United States Patent
Alinder (10) Patent No.: US 7,155,294 B2
(45) Date of Patent: Dec. 26, 2006

(54) CONDUCTOR ARRANGEMENT FOR MULTIPOLAR MEDICAL ELECTRICAL LEADS

(75) Inventor: Jason D. Alinder, Ham Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 538 days.

(21) Appl. No.: 10/606,689

(22) Filed: Jun. 26, 2003

(65) Prior Publication Data

US 2004/0267342 A1 Dec. 30, 2004

(51) Int. Cl.
*A61N 1/05* (2006.01)

(52) U.S. Cl. .................. 607/127; 607/116; 607/122; 600/375; 600/377

(58) Field of Classification Search ............... 607/122, 607/127, 116, 119, 123, 37; 600/374, 375, 600/377, 393
See application file for complete search history.

(56) References Cited

U.S. PATENT DOCUMENTS

| | | | |
|---|---|---|---|
| 4,559,951 A * | 12/1985 | Dahl et al. ............... 600/374 |
| 4,624,265 A | 11/1986 | Grassi ...................... 128/784 |
| 4,640,983 A * | 2/1987 | Comte .................... 174/119 R |
| 5,398,683 A | 3/1995 | Edwards et al. .......... 128/642 |
| 5,483,022 A | 1/1996 | Mar | |
| 5,522,874 A | 6/1996 | Gates | |
| 5,760,341 A | 6/1998 | Laske et al. | |
| 6,077,227 A | 6/2000 | Miesel et al. | |
| 6,099,524 A * | 8/2000 | Lipson et al. ............. 606/41 |
| 6,245,020 B1 | 6/2001 | Moore et al. | |
| 6,277,077 B1 | 8/2001 | Brisken et al. | |
| 6,463,334 B1 | 10/2002 | Flynn et al. ............. 607/127 |
| 6,671,562 B1* | 12/2003 | Osypka et al. ............ 607/120 |
| 2001/0012958 A1 | 8/2001 | Audoglio ................ 607/123 |
| 2002/0035319 A1 | 3/2002 | Spehr et al. ............. 600/374 |
| 2002/0143380 A1 | 10/2002 | Dahl et al. | |

* cited by examiner

*Primary Examiner*—Kennedy Schaetzle
(74) *Attorney, Agent, or Firm*—Carol F. Barry; Girma Wolde-Michael (57) ABSTRACT

A medical electrical lead includes a first electrode and a second electrode positioned distal to the first electrode; a first portion of a first cable conductor extends through a channel of the first electrode to couple with the second electrode and a second cable conductor, insulated from the first cable conductor and coupled to the first electrode, is wound about a second portion of the first cable which extends proximally from the first portion.

18 Claims, 8 Drawing Sheets

CONDUCTOR ARRANGEMENT FOR MULTIPOLAR MEDICAL ELECTRICAL LEADS

TECHNICAL FIELD

The present invention generally relates to leads for implantable medical devices, and more particularly relates to conductor arrangements for multipolar medical electrical leads.

BACKGROUND

An implantable medical device (IMD), such as a pacemaker or cardioverter-defibrillator, typically includes one or more medical electrical leads. For convenience, all types of implantable medical devices will be referred to herein as IMDs, it being understood that the term, unless otherwise indicated, is inclusive of an implantable device capable of administering any of a number of therapies to the heart or other organs or other tissue of the patient.

Electrodes, coupled to a distal portion of each lead, are implanted in a body in order to sense electrical activity and to deliver therapy from the IMD to a target site within the body. A lead body, typically constructed having an outer polymeric sheath, carries elongated conductors insulated from one another and coupling the electrodes to contacts of a lead connector that are in turn coupled to an IMD.

Arrangements of elongated conductors, typically formed from coiled or cabled wires, within the lead body are important for methods of manufacturing of the lead, methods of implanting of the lead and to the overall function and performance of the lead. Accordingly, it is desirable to provide a conductor arrangement within a lead body which facilitates manufacturing, maintains a low-profile of the lead body and reliably conducts electrical signals from the IMD to the lead electrodes over the term of implant. Characteristics of the present invention will become apparent from the subsequent detailed description of exemplary embodiments and the appended claims.

BRIEF DESCRIPTION OF THE DRAWINGS

The present invention will hereinafter be described in conjunction with the following drawing figures, wherein like numerals denote like elements.

FIGS. 5A–B are plan views

DETAILED DESCRIPTION

The following detailed description is merely exemplary in nature and is not intended to limit the invention or the application and uses of the invention.

Figure 1A:
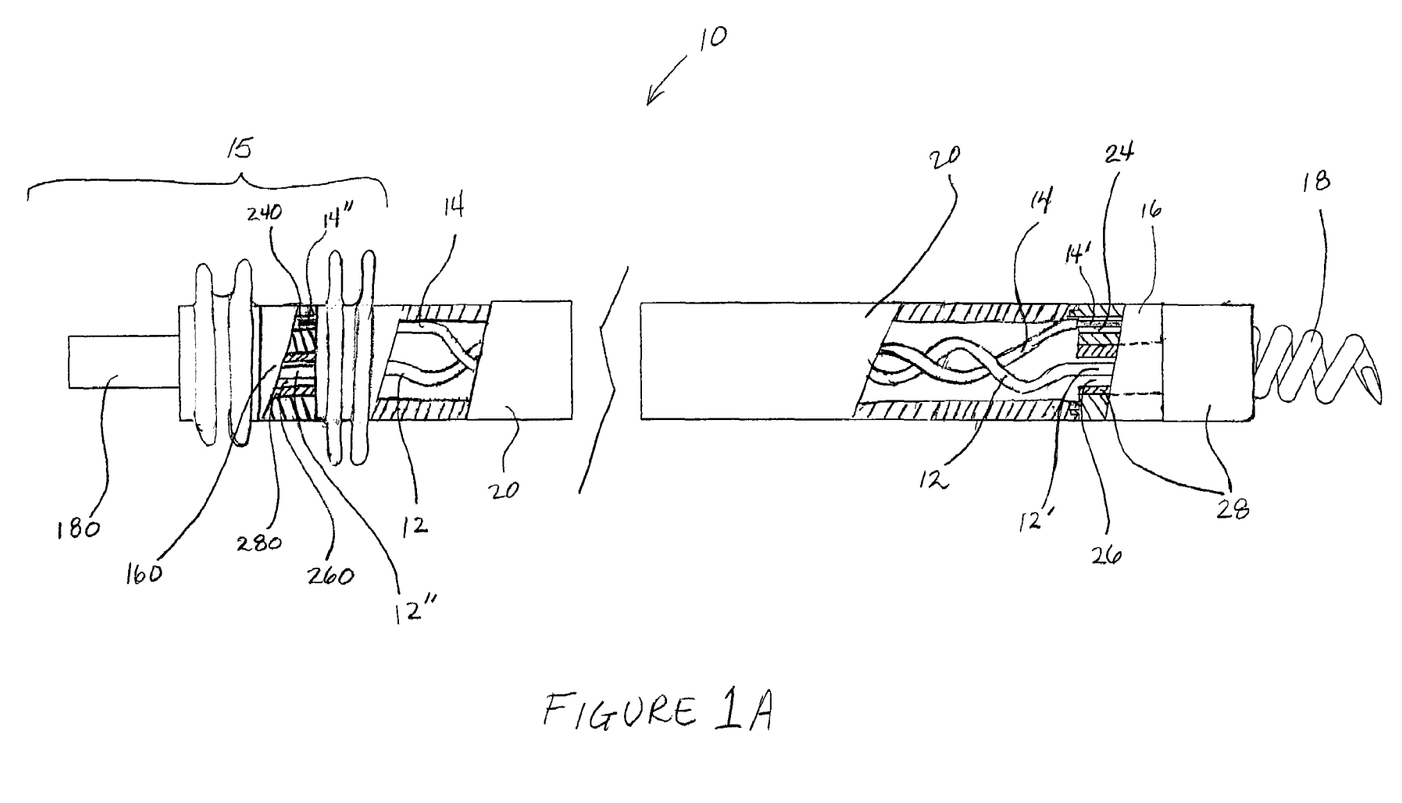
FIG. 1A is a plan view with partial sections of a bipolar medical electrical lead according to embodiments of the present invention.

FIG. 1A is a plan view with partial sections of a bipolar medical electrical lead 10 according to embodiments of the present invention. FIG. 1A illustrates lead 10 including a lead body 20 terminated at a proximal end by a pair of contacts: a pin contact 180 and a ring contact 160 forming a connector 15; and terminated at a distal end by a pair of electrodes: a tip electrode 18 and a ring electrode 16. Connector 15 may take the form of any appropriate connector, a standard connector of this type conforming to the IS-1 standard. Lead body 20 is formed of a biocompatible and biostable insulative material, for example silicone or polyurethane, known to those skilled in the art of lead construction. FIG. 1A further illustrates an elongated insulated cable conductor 12, extending along a length of lead body 20, coupling pin contact 180 to tip electrode 18, and an elongated insulated cable conductor 14, also extending along the length of lead body 20, coupling ring contact 160 to ring electrode 16; ring contact 160 and ring electrode 16 each include channels 260 and 26, respectively, through which portions of cable conductor 12 pass.

According to some embodiments of the present invention cable conductors 12 and 14 are wound one about the other within lead body 20. In the embodiment illustrated in FIG. 1A, cable 14 includes ends 14' and 14" stripped of insulation and joined to ring electrode 16, within a bore 24, and ring contact 160, within a bore 240, respectively, while cable 12 includes portions 12' and 12" passing through channels 26 and 260, respectively, of ring electrode 16 and ring contact 160, respectively, to be joined with tip electrode 18 and pin contact 180, respectively. FIG. 1A further illustrates a spacer 28, separating tip electrode 18 from ring electrode 16, including a projection into channel 26 creating a insulative lining for channel 26, according to one embodiment.

Means for joining ends 14' and 14" of cable 14 and ends of cable 12 (not shown) include methods known to those skilled in the art, for example welding, crimping and staking. Furthermore general construction of electrodes 16 and 18 and materials from which they are formed may be selected from any known to those skilled in the art; although tip electrode 18 is shown as a helix electrode in FIG. 1, it may take on a form of other tip electrodes known to those skilled in the art, for example a substantially dome-shaped form.

Figure 1B:
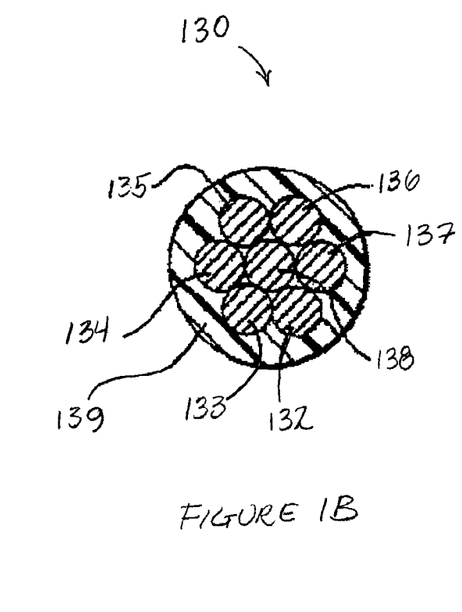
FIGS. 1B–C are radial cross-sections of alternate cable configurations that may be implemented in conjunction with embodiments the present invention.
Figure 1C:
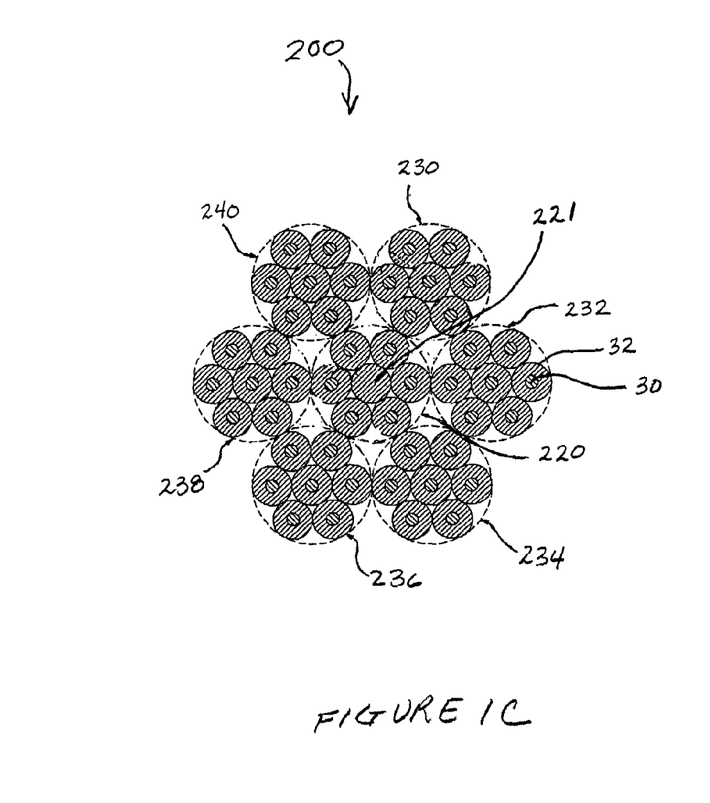

FIGS. 1B–C are radial cross-sections of alternate cable configurations that may be implemented in conjunction with embodiments the present invention, for example as insulated cable conductors 12 and 14 illustrated in FIG. 1A. FIG. 1B illustrates a cable configuration 130 including peripheral wire strands 132 through 137 formed about a core wire strand 138, any or all of which strands may be formed from a Co—Ni—Cr—Mo alloy, MP35N, or any other conductive corrosion-resistant and biocompatible material of sufficient strength and toughness; a diameter of each wire strand in various embodiments is between approximately 0.0005 inch and 0.005 inch. Using a conventional stranding machine, wire strands 132–138 are each tightly bundled in a cable-like fashion; a lay or pitch of stranding is typically between 0.3 inch and 0.6 inch. As is further illustrated in FIG. 1B, cabled configuration 130 includes an insulating coating 139 surrounding bundled wire strands 132–138. FIG. 1C illustrates a cable configuration 200 including a core wire bundle 220, formed of seven wire strands, and a number of perimeter wire strand bundles 230, 232, 234, 236, 238 and 240 helically wound about core wire strand bundle 220 without overlapping one another and at a relatively constant and shallow pitch to form a relatively constant outer diameter, which, according to various embodiments, is between approximately 0.005 inch and approximately 0.020 inch. Core wire strand bundle 220 can be referred to as a 1×N cable, i.e., a 1×7 cable in the embodiment depicted and each perimeter wire strand bundle 230, 232, 234, 236, 238, 240 is similarly formed of N, in this example 7, wires including a core wire strand and N−1, or 6, second peripheral wire strands helically wound about the core wire in a manner as described above. A method of assembling a cable configuration 200 and other considerations, such as the relative diameters of wires included, is described in U.S. Pat. No. 5,760,341, issued to Laske et al., the teachings of which are incorporated herein. As is further illustrated in FIG. 1C, with the exception of a core wire strand 221 of bundle 220, all the wire strands include a core, for example core 30 of wire strand 32; according to some embodiments of the present invention, wire strand cores are formed of a relatively low resistance material, for example gold or silver.

Figure 2A:
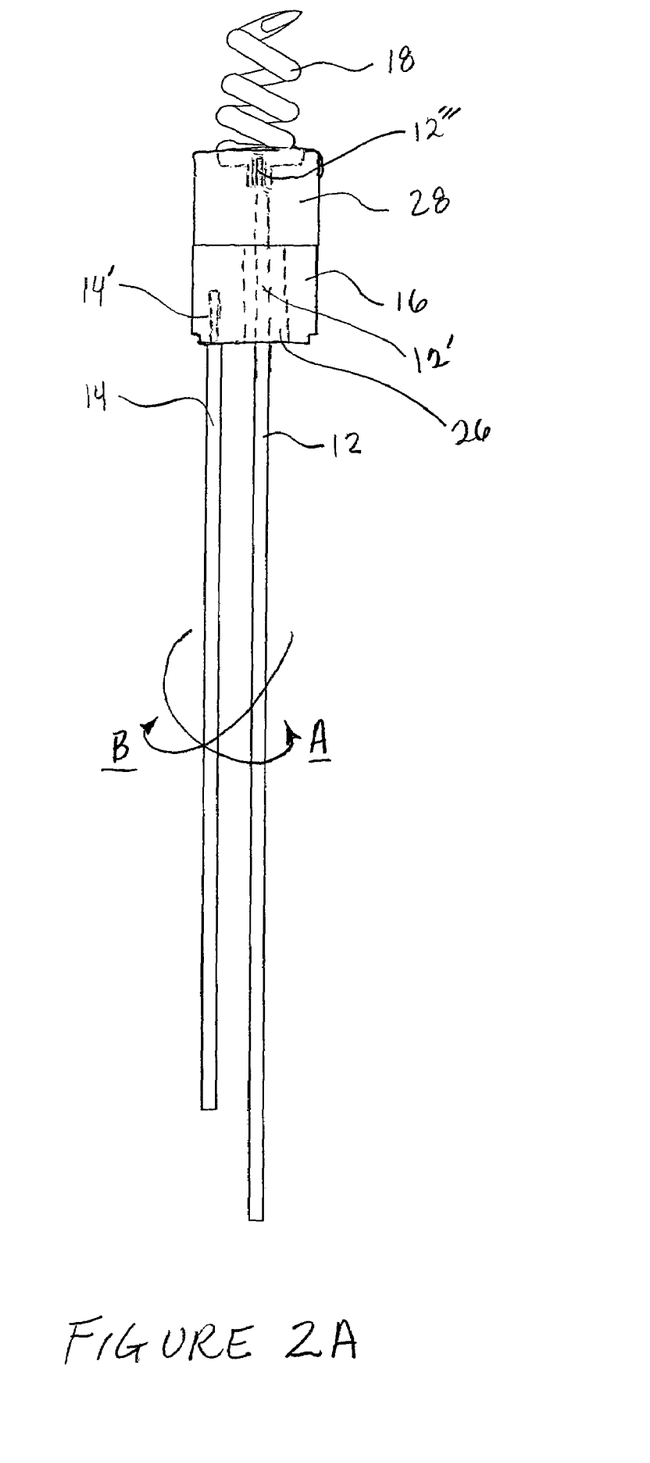
FIG. 2A is a plan view of a partial lead assembly according to embodiments of the present invention.
Figure 2B:
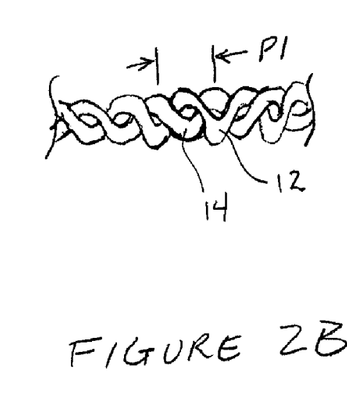
FIGS. 2B–C are partial plan views of alternate conductor configurations according to the present invention.
Figure 2C:
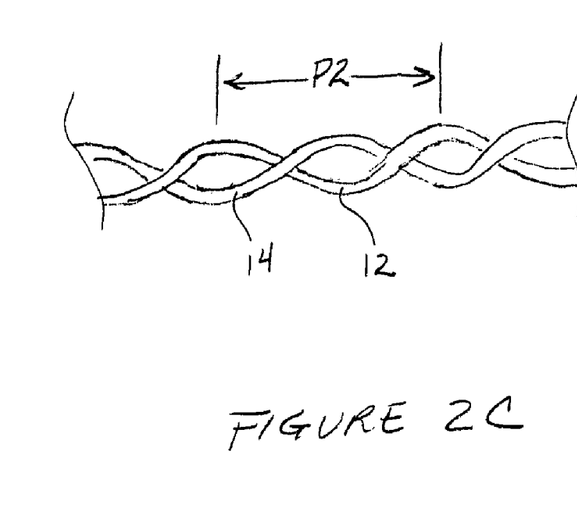

FIG. 2A is a plan view of a partial lead assembly according to embodiments of the present invention. FIG. 2A illustrates insulated cable 14 extending proximally from stripped end 14', where end 14' is joined to ring electrode 16, and insulated cable 12 likewise extending proximally from ring electrode 16, where portion 12' passes through channel 26 (shown with dashed lines); portion 12' further passes through spacer 28 and is joined to tip electrode at a stripped end 12''' (shown with dashed lines). According to embodiments of the present invention, once insulated cable conductors 14 and 12 are joined to respective electrodes, proximally extending portions of the insulated cables are wound about one another per arrows A and B illustrated in FIG. 2A. According to various embodiments, winding cables 12 and 14 about one another may result in a pitch ranging from relatively loose to relatively tight and the pitch may vary along a length of lead body 20 (FIG. 1A). FIGS. 2B–C are partial plan views of alternate conductor configurations according to the present invention wherein FIG. 2B illustrates a relatively tight wind of insulated cables 12 and 14 having a pitch, P1, and FIG. 2C illustrates a relatively loose wind of insulated cables 12 and 14 having a pitch, P2.

Figure 3:
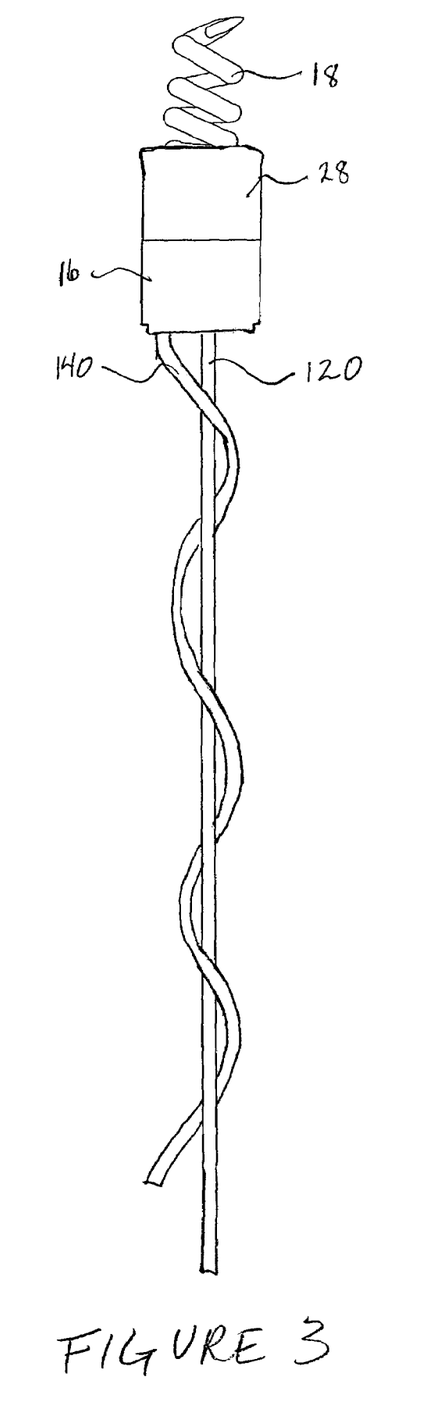
FIG. 3 is a plan view of a partial lead assembly according to an alternate embodiment of the present invention.
Figure 4:
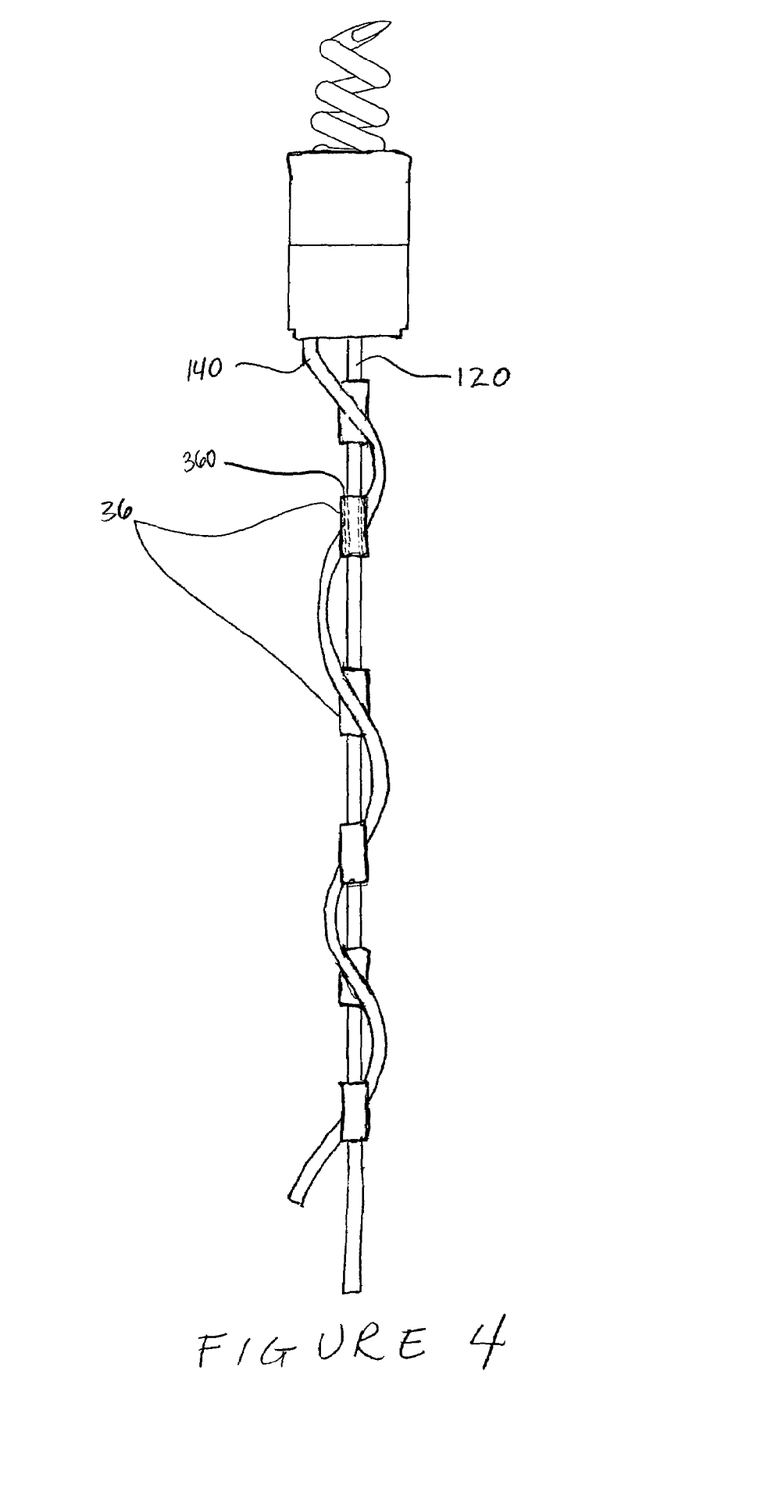
FIG. 4 is a plan view of a partial lead assembly of yet another embodiment including guides.

FIG. 3 is a plan view of a partial lead assembly according to an alternate embodiment of the present invention. FIG. 3 illustrates an insulated cable 140 extending proximally from ring electrode 16 (—a stripped end is joined to ring electrode 16 in a manner similar to that previously described) and winding about a substantially straight insulated cable 120, likewise extending proximally from ring electrode 16 (—a portion of cable 120 passes distally through a channel of ring electrode 16 and spacer 28 and is joined to tip electrode 18 as previously described). FIG. 4 is a plan view of the partial lead assembly of FIG. 3 according to yet another embodiment including guides 36, wherein guides 36 provide an interface between insulated cables 120 and 140 and may further function to hold a relative position of insulated cables 120 and 140. As illustrated in FIG. 4, according to embodiments of the present invention, each guide 36 includes a channel 360 (shown with dashed lines) for passage of insulated cable 120; in one embodiment, channel 360 includes a lubricious surface interfacing with cable 120 and, in another embodiment, guides 36 are affixed to cable 120 via channel 360. Further embodiments include guides affixed to both cables 120 and 140 and guides just affixed to cable 140 including a lubricious channel interfacing with cable 120. A lubricious surface of channel 360 may be formed via a PTFE coating or a material from which guide 36 is made may be inherently lubricious.

Figure 5A:
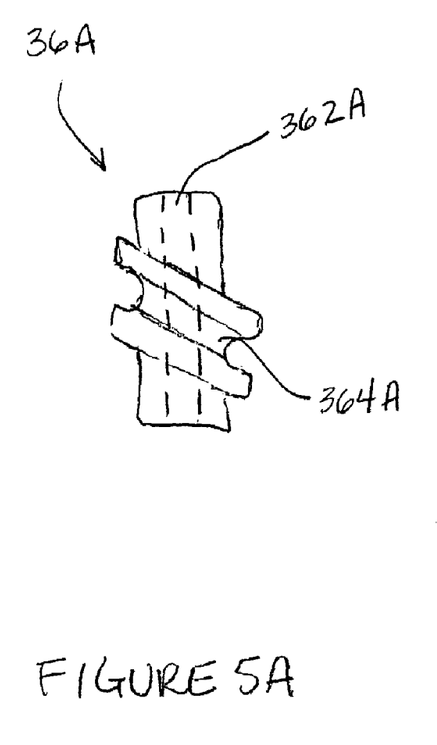
FIGS. 5A–B are plan views of exemplary guide components.
Figure 5B:
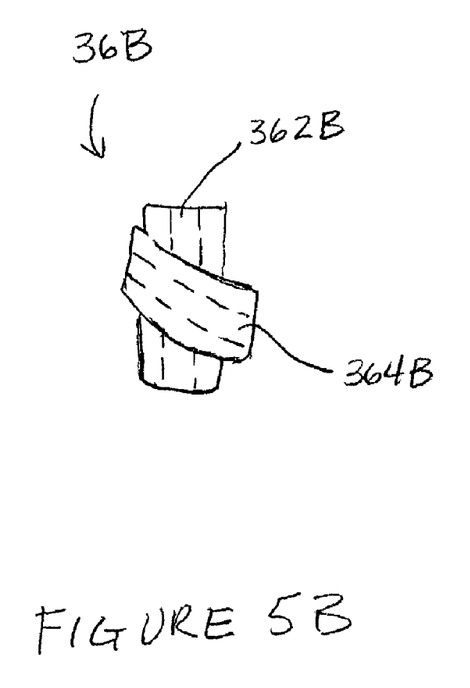

FIGS. 5A–B are plan views of further exemplary guide components. FIG. 5A illustrates guide component 36A including a first channel 362A (shown with dashed lines) for passage of a first cable, for example insulated cable 120 illustrated in FIG. 4, and a second channel 364A for passage of a second cable, for example cable 140 illustrated in FIG. 4. FIG. 5B illustrates guide component 36B including a first channel 362B (shown with dashed lines) for passage of a first cable, for example insulated cable 120 illustrated in FIG. 4, and a second channel 364B (also shown with dashed lines) for passage of a second cable, for example cable 140 illustrated in FIG. 4. Each channel of guide components, according to the present invention, may be an enclosed lumen, for example channels 362A, 362B, and 364B or have open sides, for example channel 364A; furthermore either cable of a pair of cables may be routed through either of the two channels. According to alternate embodiments, guides 36, 36A, 36B are made from materials including, but not limited to, rigid plastics, soft polymers, and ceramics.

Figure 6:
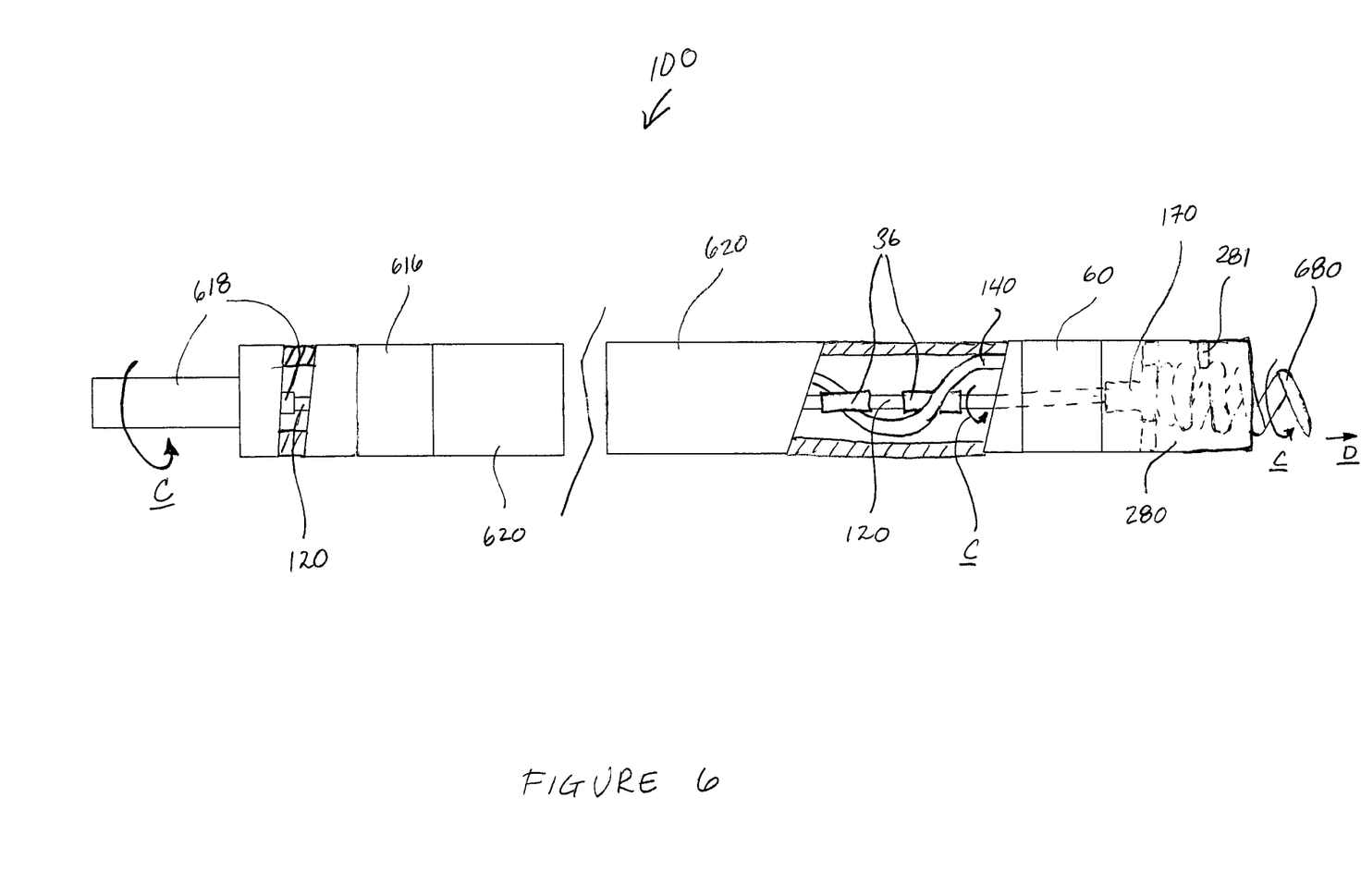
FIG. 6 is a plan view with partial sections of a bipolar lead according to alternate embodiments of the present invention.

FIG. 6 is a plan view with partial sections of a bipolar lead 100 according to alternate embodiments of the present invention. FIG. 6 illustrates lead 100 including ring electrode 60 and an extendable-retractable helix electrode 680 separated from ring electrode 60 by a spacer sleeve 280 and coupled to a pin contact 618 via insulated cable conductor 120; ring electrode 60 is coupled to a ring contact 616 via insulated cable conductor 140 as previously described for ring electrode 16 and ring contact 160 illustrated in FIG. 1A. FIG. 6 further illustrates a lead body 620 enclosing cables 120, 140 and cable 140 wound about cable 120 with guides 36 positioned between cables 140 and 120 as previously illustrated in FIG. 4. According to embodiments of the present invention, helix 680 is extended and retracted by turning pin contact 618 per arrow C; cable 120, coupling pin contact 618 and helix 680 and being supported by cable 140 and associated guides 36, transfers torque to extend helix 680 out of spacer sleeve 280 per arrow D. In this embodiment, guides include a lubricious channel 360 (FIG. 4) so that cable 120 may rotate freely therein; cable 120 may be held in an additional channel of guides 36 or may be otherwise affixed to guides 36. Finally, spacer sleeve 280 includes a tooth 281 (shown with dashed lines) or another type of guide interfacing with helix 680 in order to translate rotation per arrow C to translation per arrow D; alternative designs of spacer sleeves to accomplish this purpose are well known to those skilled in the art.

While several exemplary embodiments have been presented in the foregoing detailed description, it should be appreciated that a vast number of variations exist. Therefore, it should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing the exemplary embodiment or exemplary embodiments. It should be understood that various changes can be made in the function and arrangement of elements without departing from the scope of the invention as set forth in the appended claims and the legal equivalents thereof.

What is claimed is:

1. A medical electrical lead, comprising:
   a first electrode including a channel extending therethrough;
   a second electrode positioned distal to the first electrode;

a first cable conductor including a first portion terminated in a first end and a second portion extending proximally from the first portion; the first portion of the first cable conductor extending through the channel of the first electrode and the first end of the first cable conductor coupled to the second electrode;
a second cable conductor insulated from the first cable conductor, wound about the second portion of the first cable conductor and including a first end coupled to the first electrode; and
a plurality of guides positioned along the second portion of the first cable, each of the plurality of guides includes a channel.

2. The medical electrical lead of claim 1, wherein the second portion of the first conductor is wound about the second cable conductor.

3. The medical electrical lead of claim 1, wherein one or both of the first cable conductor and the second cable conductor further includes a bundle of wire strands, the bundle of wire strands including a core wire strand and a plurality of peripheral wire strands wound about the core wire strand.

4. The medical electrical lead of claim 3, wherein one or more of wire strands of the bundle of wire strands includes a relatively low resistance core.

5. The medical electrical lead of claim 3, wherein the one or both of the first cable conductor and the second cable conductor further includes a plurality of peripheral bundles of wire strands wound about the bundle of wire strands; each of peripheral bundles of wire strands including a core wire strand and a plurality of peripheral wire strands wound about the core wire strand.

6. The medical electrical lead of claim 3, wherein the one or both of the first cable conductor and the second cable conductor further includes an insulative coating formed about the bundle of wire strands.

7. The medical electrical lead of claim 1, further comprising the plurality of guides positioned along the second portion of the first cable providing an interface between the second cable and the first cable.

8. The medical electrical lead of claim 7, the second portion of the first cable passes through the channel.

9. The medical electrical lead of claim 8, wherein each of the plurality of guides further includes a second channel in which the second cable passes.

10. The medical electrical lead of claim 8, wherein the channel of each of the plurality of guides includes a lubricious surface interfacing with the first cable.

11. The medical electrical lead of claim 1, wherein the channel of the first electrode includes an insulative lining.

12. The medical electrical lead of claim 1, further comprising:
a connector contact including a channel extending therethrough;
a connector terminal pin; and
wherein the first cable conductor further includes a third portion extending proximally from the second portion and terminated by a second end; the third portion passing through the channel of the connector contact and the second end coupled to the connector terminal pin; and
the second cable conductor further includes a second end coupled to the connector contact.

13. A medical electrical lead, comprising:
a first electrode including a channel extending therethrough;
a second electrode positioned distal to the first electrode;
a first cable conductor including a first portion terminated in a first end and a second portion extending proximally from the first portion; the first portion of the first cable conductor extending through the channel of the first electrode and the first end of the first cable conductor coupled to the second electrode;
a second cable conductor insulated from the first cable conductor, wound about the second portion of the first cable conductor and including a first end coupled to the first electrode;
the plurality of guides positioned along the second portion of the first cable
providing an interface between the second cable and the first cable wherein each of the plurality of guides is affixed to the first cable.

14. A medical electrical lead, comprising:
a first electrode including a channel extending therethrough;
a second electrode positioned distal to the first electrode;
a first cable conductor including a first portion terminated in a first end and a second portion extending proximally from the first portion; the first portion of the first cable conductor extending through the channel of the first electrode and the first end of the first cable conductor coupled to the second electrode;
a second cable conductor insulated from the first cable conductor, wound about the second portion of the first cable conductor and including a first end coupled to the first electrode;
the plurality of guides positioned along the second portion of the first cable
providing an interface between the second cable and the first cable wherein each of the plurality of guides is affixed to the second cable.

15. A medical electrical lead comprising:
a first electrode including a channel extending therethrough;
a second electrode positioned distal to the first electrode;
a first cable conductor including a first portion terminated in a first end and a second portion extending proximally from the first portion; the first portion of the first cable conductor extending through the channel of the first electrode and the first end of the first cable conductor coupled to the second electrode; a second cable conductor insulated from the first cable conductor, wound about the second portion of the first cable conductor and including a first end coupled to the first electrode;
a connector contact including a channel extending therethrough;
a connector terminal pin;
wherein the first cable conductor further includes a third portion extending proximally from the second portion and terminated by a second end; the third portion passing through the channel of the connector contact and the second end coupled to the connector terminal pin;
the second cable conductor further includes a second end coupled to the connector contact; and
a plurality of guides positioned along the second portion of the first cable providing an interface between the second cable and the first cable.

16. The medical electrical lead of claim 15, wherein each of the plurality of guides includes a channel in which the second portion of the first cable passes.

17. The medical electrical lead of claim 16, wherein the channel of each of the plurality of guides includes a lubricious surface interfacing with the first cable.

18. The medical electrical lead of claim 17, wherein the second electrode forms an extendable/retractable helix being extended and retracted by the first cable via rotation of the connector terminal pin.

* * * * *